United States Patent
Mellinger et al.

(12) 
(10) Patent No.: US 6,302,888 B1
(45) Date of Patent: Oct. 16, 2001

(54) LOCKING DOVETAIL AND SELF-LIMITING SET SCREW ASSEMBLY FOR A SPINAL STABILIZATION MEMBER

(75) Inventors: Philip A. Mellinger, Las Flores, CA (US); Donald B. Knoth, Dayton, OH (US)

(73) Assignee: Interpore Cross International, Irvine, CA (US)

( * ) Notice: Subject to any disclaimer, the term of this patent is extended or adjusted under 35 U.S.C. 154(b) by 0 days.

(21) Appl. No.: 09/272,493

(22) Filed: Mar. 19, 1999

(51) Int. Cl.[7] .................................................. A61B 17/86
(52) U.S. Cl. .................. 606/73; 606/61; 411/5; 411/393; 411/405; 411/910
(58) Field of Search ................ 606/60, 61, 72, 606/73; 411/1, 2, 3, 393, 380, 402, 403, 405, 410, 5, 910

(56) References Cited

U.S. PATENT DOCUMENTS

| | | | |
|---|---|---|---|
| 2,180,633 | * 11/1939 | Holt . | |
| 4,347,845 | 9/1982 | Mayfield . | |
| 4,887,596 | 12/1989 | Sherman | 606/61 |
| 5,257,993 | 11/1993 | Asher et al. | 606/61 |
| 5,360,431 | 11/1994 | Puno et al. | 606/72 |
| 5,380,326 | * 1/1995 | Lin | 606/61 |
| 5,607,426 | 3/1997 | Ralph et al. | 606/61 |
| 5,615,965 | 4/1997 | Saurat et al. | 403/24 |
| 5,630,817 | 5/1997 | Rokegem et al. | 606/61 |
| 5,669,911 | 9/1997 | Errico et al. | 606/61 |
| 5,697,929 | 12/1997 | Mellinger | 606/61 |
| 5,702,395 | 12/1997 | Hopf | 606/61 |
| 5,944,720 | 8/1999 | Lipton | 606/61 |

FOREIGN PATENT DOCUMENTS

| | | |
|---|---|---|
| 410 7480 | 3/1991 | (DE) . |
| 2723837 | 2/1994 | (FR) . |

* cited by examiner

Primary Examiner—Michael Buiz
Assistant Examiner—David O. Reip
(74) Attorney, Agent, or Firm—Hudak & Shunk Co., L.P.A.; Laura F. Shunk

(57) ABSTRACT

A spinal implant assembly is provided which has a stabilizer rod clamped into position within an anchor by means of a sliding closure member including a mating set screw or hook. The exterior faces of the anchor are contoured to optimize interface in the surgical setting. The anchor includes a U-shaped channel having multiple undercut surfaces such as grooves, which mate with flange like projections or "dovetails" of a closure member which is slid in a direction corresponding to the longitudinal axis of the rod. The closure member has on either side a flange mating with opposing recesses formed at the top of the U-shaped channel so as to lock the closure member in place. The set screw has an external hex head for tightening, and a plurality of radically extending prongs which are undercut and which mate with the recesses in the top of the U-shaped channel of the anchor. The hex head sheers at a necked area above the radial collar to provide for a flush surface relative to the closure member. The undercuts on the prongs allow the set screw to be unscrewed from the closure member.

19 Claims, 3 Drawing Sheets

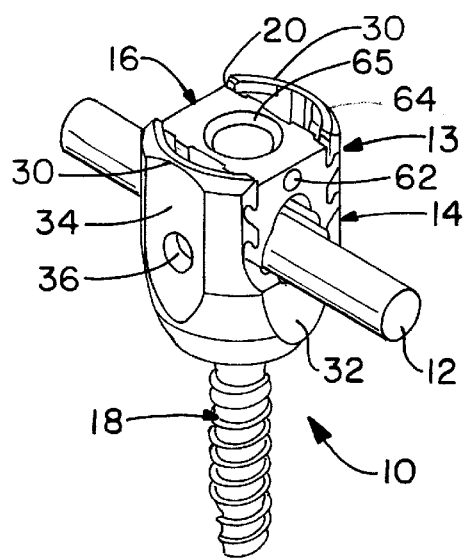
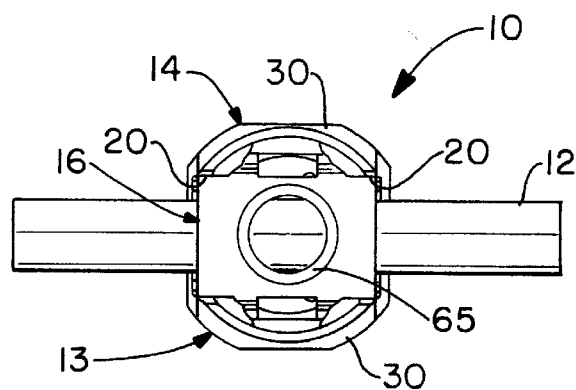
FIG.-1
FIG.-2
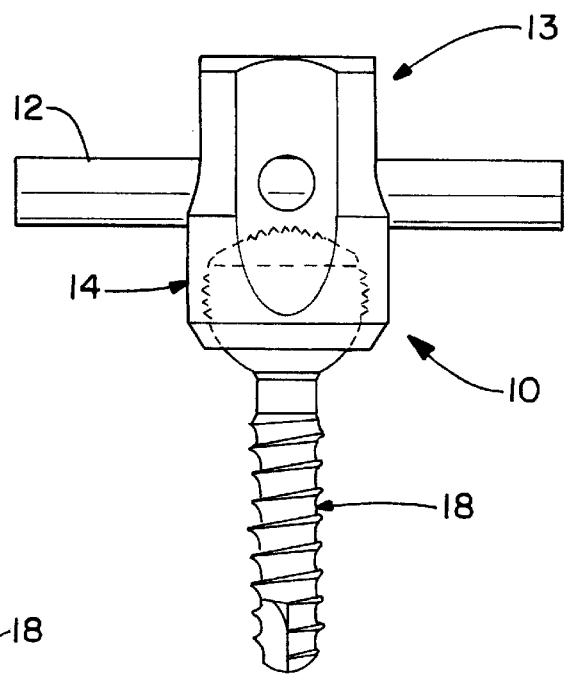
FIG.-3
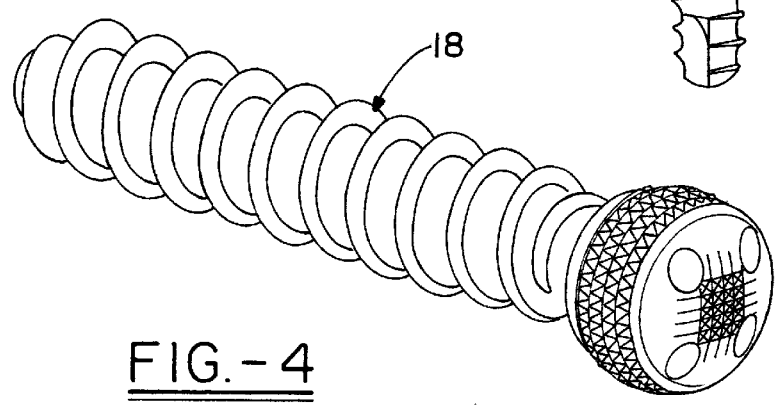
FIG.-4

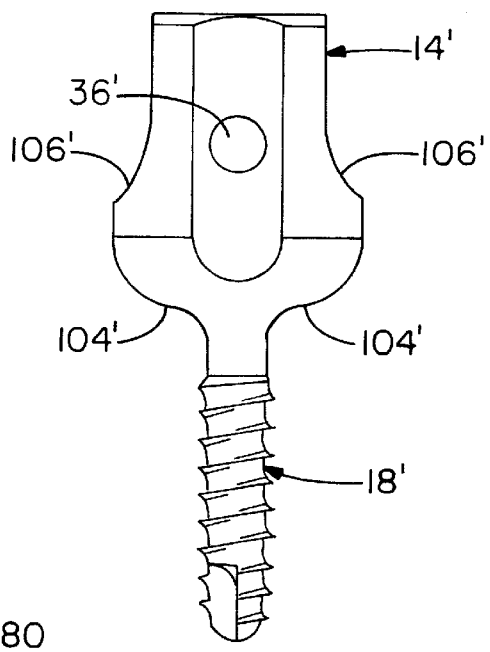
FIG.-8
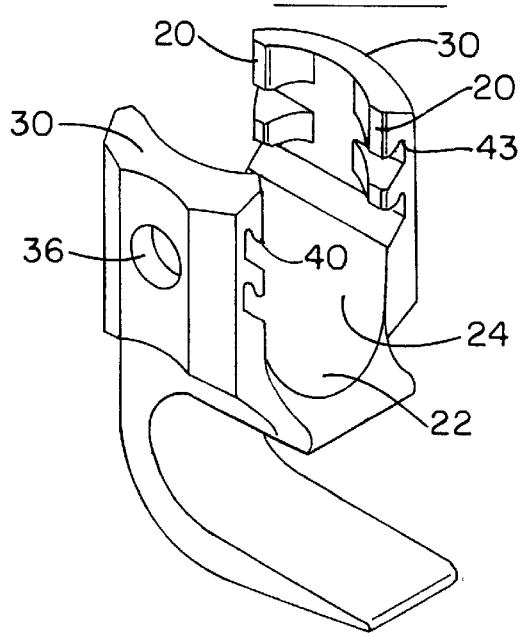
FIG.-9
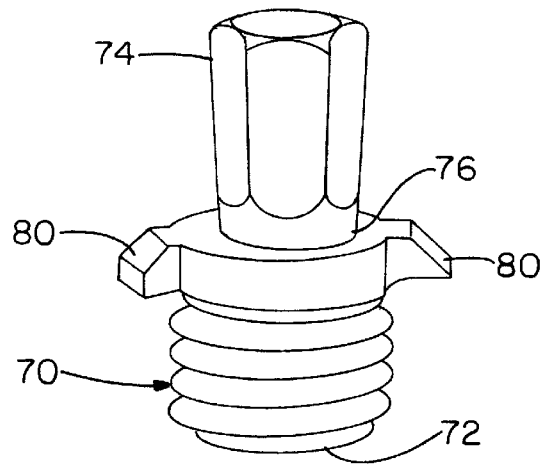
FIG.-10
FIG.-11

LOCKING DOVETAIL AND SELF-LIMITING SET SCREW ASSEMBLY FOR A SPINAL STABILIZATION MEMBER

FIELD OF THE INVENTION

The invention relates generally to an implant assembly for a manipulation and/or stabilization of a spine and generally comprises an anchor for an elongated stabilizer such as a rod, a sliding locking member which cooperates with the anchor so as to capture the stabilizer within the anchor and a shear off set screw having removal means.

BACKGROUND OF THE INVENTION

It has become accepted for certain medical indications to stabilize the relative position of vertebrae for at least some limited period of time. Anchor members are attached onto vertebral bodies, such as in the case of laminar hooks, or are implanted into the bodies using screw members. The anchors generally include means to hold a rod such as a clamping means which forms an integral part of the anchor. Adjacent anchors customarily hold respective vertebrae relative to a stabilizer, i.e. a plate or a rod.

In reciting the objectives of an assembly, it is critical to keep the biological context in mind. Thus, it is important not only to achieve the desired load limitations and stabilization characteristics, but also to design a series of components and respective instrumentation which is as easily manipulated and as quickly assembled as possible, which is as non-obtrusive into the biological environment as possible, and which is designed with the goal of avoiding failure. A surgeon may have limited physical access to the surgical site as well as obscured surgical visibility. It is critical to avoid the pieces or filings which could fall into a wound site. It is also important to design a system which can be manipulated by a gloved surgeon.

It is also desirable to have a system designed to allow as much flexibility for the surgeon as possible and yet to include some self-limiting features in order to maintain ease of application.

It is therefore an object of the current invention to provide a stabilizer anchor member having a closure means, which slides into position to capture an elongated stabilizer within the anchor member. The sliding closure means is designed to provide increased resistance to spreading of the anchor member.

It is a further object of the invention to provide a novel set screw which is self limiting and can achieve a higher torque. Moreover, the set screw allows for a gradual transition shear rather than a sudden snapping.

In addition, the set screw includes external prongs to mate with a removal instrument for removal of the set screw after shear.

SUMMARY OF THE INVENTION

The invention relates to a spinal implant assembly including an elongated stabilizer which is preferably a rod but could include a plate or cable, and anchor means which are secured relative to a spinal bone member and which include clamping means which secure the stabilizer relative to the anchor means. More specifically, the anchor means includes a U-shaped channel which receives a stabilizer rod. A closure member slides into position in the channel so as to capture the rod circumferentially in the channel. The channel has at least one, preferably a plurality and most preferably two undercut surfaces in each one of the two side walls of the U-shaped channels. These undercut surfaces formed for example as part of groove, define an oblique angle with respect to the side wall surface. The closure member includes multiple mating flange-like projections on each side or "dovetails" which have a corresponding configuration. These mating dovetails inhibit the spreading or splaying of the side walls of the channel in response to forces executed on the anchor assembly by the locking set screw acting on the stabilizer rod.

The closure member includes a detent means which cooperates with the anchor member. This causes the closure member to "snap" into place as it is slid into position in the channel. In particular, the closure member has a ridge, and preferably has two ridges on opposing sides, and the anchor includes a recess to receive the ridges. In particular, the anchor member includes a central bore at the top of the U-shaped channel to define opposing C-shaped areas. Correspondingly, the anchor includes integral opposing radiused recessed areas in the section of each side wall adjacent the top opening of the channel. These areas interact with the ridges so that the closure member is slid longitudinally and subsequently locked into position.

Additionally, the anchor assembly includes a self-limiting set screw received in a screw hole in the closure member. The set screw has a threaded portion with a beveled end distal to an external hexagonal head for tightening the screw. The hex head is joined to the rest of the screw by a necked area which is designed to shear at a preselected torque so that after tightening the screw does not extend beyond the anchor assembly. The screw further includes a plurality of radially projecting prongs which form a collar which fits into the recessed central bore in the top opening of the rod channel. The prongs include undercut areas designed to allow the screw to be removed after the hexagonal head has sheared off.

These undercuts provide for the screw to be self-tightening with regard to the removal instrument. The prongs of the set screw nest into a recessed central bore in the top opening of the rod channel. This prevents the closure member from disengaging the bone anchor once the set screw is tightened. Thus, the detent means, or interference fit acts as a temporary locking mechanism which will hold during manipulation such as rod rotation or distraction. In accordance with the invention, the anchor member is open, i.e. includes a top loading rod channel but can be closed to allow for considerable forces during manipulation. Thus, the invention allows the rod to be installed in the rod anchor and subsequently closed rather than requiring the anchor to be threaded on to the rod and surgically implanted while in place on the rod. The implant assembly is subsequently locked by tightening the set screw. First, the set screw is loosely positioned to hold the components together during intermediate tweaking of the assembly to achieve the desired vertebral alignment. When this has been achieved, the set screw can be tightened to lock the assembly and more specifically to lock the rod in the anchor. The set screw is subsequently sheered. During tightening of the set screw, a large force is applied to the bone anchor. Multiple dovetails of the present invention inhibits the anchor from spreading in response to the applied force. Further, the nesting fit between the shoulder of the set screw and the recess of the anchor inhibits longitudinal sliding of the closure member.

An additional key advantage of the design is that the closure member can be slid into the anchor from either side. Again, the nesting of the set screw relative to the bone anchor inhibits disengagement. The additional aspect of allowing top loading of the closure member in the bone anchor provides that the closure member has to be slid only a minimum distance, i.e. three or four millimeters, and from either direction. Consequently, the systems provide many assembly options to the surgeon.

The anchor or assembly includes means to fasten it to bone such as a hook or screw. The fastener can be integral with the anchor or assembly or can be a separate and cooperating member. For example, the anchor can include a through bore extending substantially perpendicular to the rod channel. The bore includes a rimmed bottom portion such that a screw or hook can be received in the anchor. Preferably the screw has a hemispherical or spherical head so as to form a ball and socket joint with the anchor.

As a further aspect of the invention, the screw head is at least substantially spherical. The screw head has multiple offset holes, preferably three or four to permit the screw to be implanted into the vertebrae and easily removed. The screw socket includes a high friction mating surface and the rod channel is spaced at a distance less than the diameter of the screw head from the bone contact surface so that the rod forces the screw head into a locked engagement with the screw socket high friction surface when the assembly is finally tightened.

The spherical head of the present invention allows for a maximum head position and, consequently, the greatest angulation of the screw relative to the bone anchor. In this instance, the spherical head defines a full circle to provide for a round rod contacting area i.e., the head is substantially free from a recess on the longitudinal axis. The rod hits the screw head to lock the assembly together. The present invention presents the further advantage of having "offset" driving recesses to allow the maximization of the sphere head. Preferably, three or four offset holes are provided which allow for a driving torque but maintain the maximum surface area of the spherical head while achieving the torque required or insertion. In the assembly, the rod contacts the screw head without an intermediate piece in order to lock the assembly together.

BRIEF DESCRIPTION OF THE DRAWINGS

FIG. 1 is a perspective view of the spinal implant assembly;

FIG. 2 is a top view of the implant assembly;

FIG. 3 is a side elevational view of the assembly of FIG. 1, and showing the U-shaped channel of the anchor member and spherical head of the screw member in phantom;

FIG. 4 is a perspective view of the screw member of the assembly of FIG. 3.

FIG. 8 is a side elevational view of the integral anchor of FIG. 7;

FIG. 9 is a bottom perspective view of the set screw in accordance with the invention;

FIG. 10 is a side perspective view of the set screw shown in FIG. 9;

FIG. 11 is a perspective view of the hook anchor of FIG. 6 showing the dovetail locking mechanism in further detail.

DETAILED DESCRIPTION OF THE INVENTION

Figure 5:
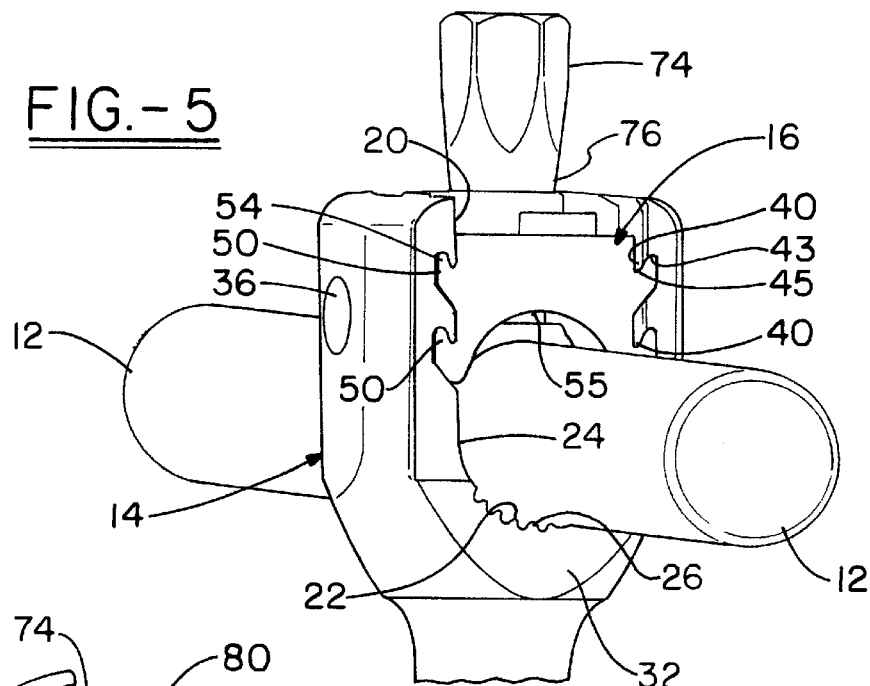
FIG. 5 is a perspective view of the implant assembly.

An implant assembly in accordance with the invention is shown generally at 10. The assembly includes a stabilizer rod 12 which is captured in an anchor assembly 13 which comprises an anchor 14, a closure member 16 and a fastener 18. In this case, the fastener is illustrated as a bone screw. It is shown as a separate element in FIGS. 1 through 6, and as an integrally formed unit in FIGS. 7 and 8.

In particular, the anchor assembly 13 is designed to encircle the stabilizer rod 12 and secure it relative to the fastener 18. An object is to provide an assembly which is easily assembled and yet which will withstand the forces which are applied during the manipulation of the spinal bodies, and also postoperatively. The assembly should be minimally invasive to the biological environment providing for a relatively low profile and contoured surfaces to avoid the possibility of postoperative irritation.

The anchor 14 includes a channel 20 which is generally U-shaped. The anchor has a top surface 64. The channel 20 has a bottom surface 22 and opposing sidewalls 24. The bottom 22 includes a rounded portion which is radiused to mate with the lower circumference of the rod, and may preferably include a high-friction surface 26 such as ridges or knurling. The anchor 14 also includes outside lateral faces 30 which face outwardly relative to the channel along the axis of the rod. A first set of vertical faces include canted areas 32 which slope inward in relation to the channel. A second pair of opposing outside vertical faces 34 each includes an opening 36 which can be used with an instrument to hold the anchor 14.

Figure 6:
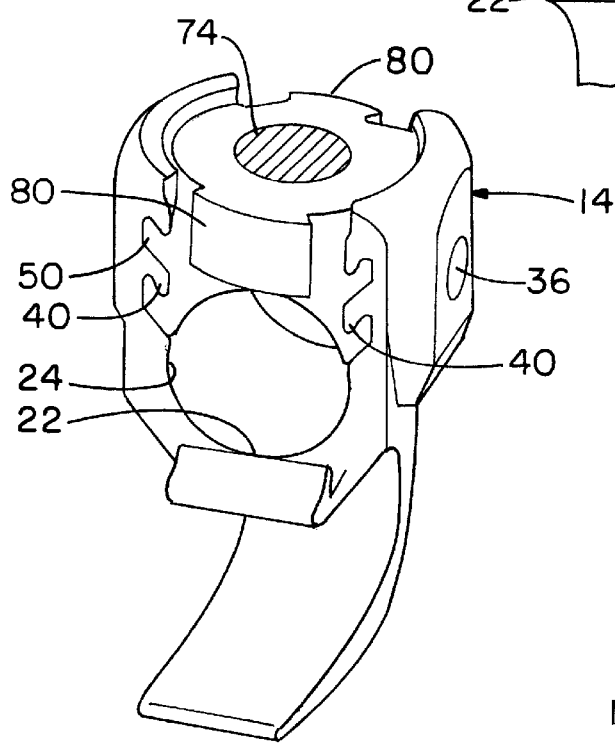
FIG. 6. is an enlarged view showing the relationship between the closure member and a hook anchor in detail after the set screw has been sheared off.

The opposing side surfaces on the inside of the U-shaped channel 20, each include multiple dovetailed-shaped grooves which cooperate with corresponding projecting flanges 40 on the sliding closure member 16. As best shown in FIG. 6, the sidewalls 24 preferably each include 2 openings having a top undercut which forms an angle of about 30° relative to the sidewall, and a bottom undercut which forms an angle of about 45° relative to the sidewall. The inside of the recess 43, and of the ridge 45 formed in the inside wall, are both slightly rounded for ease of manufacture. The closure member 16 includes two (2) outwardly projecting flange members 50, which correspond in configuration to the shape of the dovetail within the sidewall of the shaped channel.

The closure member 16 includes an arch 52 in its bottom side surface which is rounded in order to accommodate the upper rod surface. Further, the closure member includes an enlargement 53 in the arch 52 on the opposing lateral exterior faces 55 of the closing member 16. This enlargement, 53, is intended to provide for a certain amount of leveraging of the rod during bending or manipulation operations. The sliding closure member 16 further includes an elongated flange 54 on each vertical surface with the dovetails. These flanges extend in the direction corresponding to the longitudinal axis of the rod. These flanges 54 have a length "L" which corresponds to the cordal length of a radiused recessed 60 formed within the anchor member 14 at the top opening of the U-shaped channel. The flange 54 act to press the closure member outwardly slightly during the sliding activity. When the flanges 54 encounter the opening provided by the recesses 60, the sliding member clicks into a closed location.

The sliding member further includes a dimple 62 which is received in an instrument for insertion in the closure member.

In addition, the sliding member includes a bore 65 in the top which receives a set screw. The set screw is a self-limiting set screw and includes a screw area 70 having a beveled bottom 72, and an external hexagonal head 74 for screwing the set screw into place in the bore 65. The screw further includes a necked area 76, which joins the external head 74 to the threaded head 70. In addition, the screw includes a series of prongs 80, which together form a radially extending collar. There are preferably 2 to 6 prongs, and most preferably 4 prongs, each having an undercut 82 at an angle of about 30° to about 60° and preferably from 40° to 50°. An insertion tool mates with the prongs to enable the screw to be removed. During insertion, the screw is tightened until the neck area 76 sheers at a predetermined load ,i.e. of from about 45 to 100 in-lbs. Thereafter, the screw is relatively flush with respect to the bore 65. The radially extending collar formed by the flanges 80, is received in the recessed area 64 of the closure member.

Figure 7:
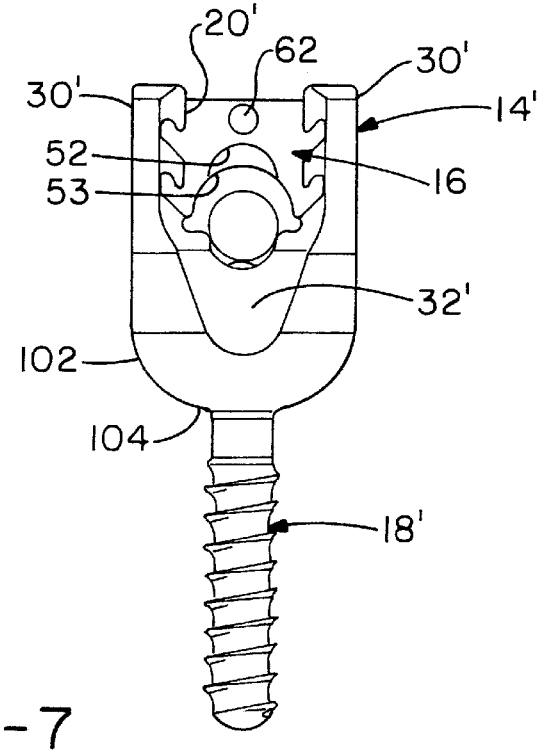
FIG. 7 is a side elevational view of an integral anchor in accordance with a second embodiment of the invention.

FIGS. 7 and 8 illustrate an embodiment of the invention which corresponds in structure to the previously described invention except that the anchor 14' and screw 18' are formed as an integral unit. The anchor 14' has a channel 20' which is generally U-shaped and includes a high-friction surface 26'. Outside lateral faces 30' face outwardly relative to the channel along the axis of the rod. A first set of vertical faces include canted areas 32' which slope inwardly in relation to the channel. The anchor 14' has a bone contacting area 14', a radiused bottom area 102, and a tapered area 106'.

In addition, in a separate embodiment of the invention, a spherical headed screw is used to secure the anchor 14 to the bone. Specifically, the screw is at least substantially spherical. This enables a great degree of freedom in the ball and socket joint between the anchor 14 and the screw. Further, the screw head includes a plurality, and preferably 2–6, most preferably 3 or 4 holes which are used to insert the screw into the bone. These are preferably offset to maximize torque on the screw. The offset refers to the fact that the screw includes at least one (and more preferably at least two) driving recesses which are not coaxial with the longitudinal axis of the fastener (i.e. the axis of rotation for insertion and removal.) More particularly, these driving recesses should be placed so as to maintain an axis of rotation for insertion which is coaxial with the longitudinal axis of the fastener and which permits an appropriate amount of torque to be applied while maximizing the surface area of the screw head to allow for the most variations of angle placement of the screw fastener. This angle is accomplished by placing the anchor in position on the screw, driving the screw into position and placing the anchor in an appropriate angular alignment to permit sufficient tightening of the fastener. FIG. 4 is shown having multiple smooth bore holes which extend approximately to the maximum diameter (in the transverse direction) of the spherical head. The insertion tool will have, for example, two prongs so that two radially aligned holes can be used. This allows the alternative use of either of two sets of holes.

The closure member is contoured by having a radiused bottom area 102 and a bone contacting area 104. The closure member includes a taper 106 to provide for less bulk in the area of the closure member.

While in accordance with the patent statutes the best mode and preferred embodiment have been set forth, the scope of the invention is not limited thereto, but rather by the scope of the attached claims.

What is claimed is:

1. A spinal implant assembly comprising a bone anchor and a fastener, said anchor including a u-shaped channel which receives a rod, said channel including two opposing parallel lateral surfaces each having at least two undercut surfaces and a closure member having two parallel longitudinal surfaces each including two flange members which dovetail into recesses defining said undercut surfaces of said anchor channel.

2. A spinal implant assembly as set forth in claim 1, wherein said channel includes a first vertical open end and a second vertical open end and said closure member can be slid in the direction of said longitudinal axis from either said first vertical open end or said second vertical open end.

3. A spinal implant assembly as set forth in claim 1, wherein said u-shaped channel has a top opening with a transverse recess and said closure member has a top surface with a threaded recess to receive a set screw which cooperates to lock said rod in position relative to said bone anchor.

4. A spinal implant assembly as set forth in claim 3, wherein said set screw includes a externally projecting area for having an external hex to drive said set screw.

5. A spinal implant assembly as set forth in claim 4, wherein said external hex area is joined by a neck portion to a threaded portion of said set screw.

6. A spinal implant assembly as set forth in claim 5, wherein said external hex area sheers at said necked portion upon the application of a force in excess of about 45 inch pounds.

7. A spinal implant assembly as set forth in claim 5, wherein said set screw further includes externally projecting prongs.

8. A spinal implant assembly as set forth in claim 7, wherein said set screw has from two to six radially projecting prongs having windowed areas in between.

9. A spinal implant assembly as set forth in claim 8, wherein said set screw prongs each have an undercut surface.

10. A spinal implant assembly as set forth in claim 9, wherein said undercut is at angle of from about 30 to about 60°.

11. A spinal implant assembly as set forth in claim 10, wherein said prongs form a radially extending collar and wherein said radially extending collar is received in the channel of the anchor.

12. A set screw for use in a spinal implant comprising a first threaded portion and a second portion having an external hexagonal cross section joined by a necked area to said first portion and further comprising an intermediate area having a plurality of prongs which together form a radially extending collar.

13. A set screw as set forth in claim 12, wherein said radially extending prongs each have an undercut area.

14. A set screw as set forth in claim 12, wherein said second portion sheers at said necked area at a load of at least about 45 inch pounds.

15. A set screw as set forth in claim 12, wherein said set screw has from about two to about six prongs.

16. A set screw as set forth in claim 15, wherein said prongs have an undercut at an angle of from about 30 to about 60°.

17. A set screw as set forth in claim 16, wherein said prongs have an undercut at an angle of from about 40 to about 50°.

18. A set screw as set forth in claim 17, wherein there are four equally radially spaced prongs.

19. A set screw as set forth in claim 18, wherein said first portion of said set screw terminates in a beveled area.

* * * * *